(12) United States Patent
Some et al.

(10) Patent No.: US 6,791,099 B2
(45) Date of Patent: Sep. 14, 2004

(54) LASER SCANNING WAFER INSPECTION USING NONLINEAR OPTICAL PHENOMENA

(75) Inventors: Daniel I. Some, Ashdod (IL); Silviu Reinhorn, Mevasseret-Zion (IL); Gilad Almogy, Givatayim (IL)

(73) Assignee: Applied Materials, Inc., Santa Clara, CA (US)

( * ) Notice: Subject to any disclaimer, the term of this patent is extended or adjusted under 35 U.S.C. 154(b) by 331 days.

(21) Appl. No.: 09/784,626

(22) Filed: Feb. 14, 2001

(65) Prior Publication Data

US 2002/0109110 A1 Aug. 15, 2002

(51) Int. Cl.$^7$ ................................................ G01V 8/00
(52) U.S. Cl. .......................... 250/559.4; 250/559.45; 356/237.2
(58) Field of Search .................... 250/559.4, 559.41, 250/559.42, 559.43, 559.01, 559.04, 559.06, 559.15; 356/237.1, 237.2, 237.3, 237.4, 237.5

(56) References Cited

U.S. PATENT DOCUMENTS

| | | | | |
|---|---|---|---|---|
| 4,532,430 A | * | 7/1985 | Ross et al. | 250/559.48 |
| 4,692,690 A | * | 9/1987 | Hara et al. | 356/394 |
| 5,399,867 A | * | 3/1995 | Kohno | 250/461.1 |
| 5,822,055 A | * | 10/1998 | Tsai et al. | 356/237.1 |
| 5,936,726 A | * | 8/1999 | Takeda et al. | 356/237.2 |
| 6,067,154 A | * | 5/2000 | Hossain et al. | 356/237.2 |

OTHER PUBLICATIONS

PCT International Search Report dated Sep. 27, 2002.
"Application of Room Temperature Photoluminescence for the Characterization of Impurities and Defects in Silicon", V. Higgs et al., Electrochemical Society Proceedings, Sep. 13, 1999, vol. 99–16, pp. 21–37.
International Preliminary Examination Report dated Jun. 2, 2003.

* cited by examiner

Primary Examiner—David V. Bruce
Assistant Examiner—Hoon Song
(74) Attorney, Agent, or Firm—McDermott Will & Emery

(57) ABSTRACT

An optical inspection apparatus and method is provided that utilizes both linear and nonlinear optical phenomena to detect defects. Embodiments include irradiating a portion of the surface of an article, such as a semiconductor device, with a light beam, such as a scanning laser at an incident wavelength. The light emanating from the irradiated surface portion is then separated into light at the incident wavelength and light at one or more predetermined non-incident wavelengths, as by a diffraction grating, prism or filters. The light at the incident and nonincident wavelengths is sent to separate detectors, such as photomultipliers (PMT), which respectively convert the detected linear optical phenomena (representing, e.g., surface topography) into an electrical signal, and the detected nonlinear optical phenomena, such as fluorescence, Raman scattering and/or second harmonic generation, into electrical signals representing, e.g., chemical composition and material interfaces. The signal from each detector is sent to a processor, which generates a defect map based on the information gleaned from both the linear and nonlinear optical phenomena.

32 Claims, 4 Drawing Sheets

LASER SCANNING WAFER INSPECTION USING NONLINEAR OPTICAL PHENOMENA

FIELD OF THE INVENTION

The present invention relates to a method and apparatus for inspecting the surface of an article. The present invention has particular applicability for in-process inspection of semiconductor wafers during manufacture of high density semiconductor devices with submicron design features, and for inspection of reticles used for semiconductor device manufacture.

BACKGROUND ART

Current demands for high density and performance associated with ultra large scale integration require submicron features, increased transistor and circuit speeds and improved reliability. Such demands require formation of device features with high precision and uniformity, which in turn necessitates careful process monitoring, including frequent and detailed inspections of the devices while they are still in the form of semiconductor wafers.

Conventional in-process monitoring techniques employ an "inspection and review" procedure wherein the surface of the wafer is initially scanned by a high-speed, relatively low-resolution inspection tool; for example, such a tool can include a laser and an opto-electric converter such as a CCD (charge-coupled device). Statistical methods are then employed to produce a defect map showing suspected locations on the wafer having a high probability of a defect. Typically, after a redetection procedure is carried out, using the defect map, to positively determine the presence of defects, a more detailed review procedure is carried out on the individual defect sites, such as with a scanning electron microscope (SEM) to produce a relatively high-resolution image. The defect image is then analyzed to determine the nature of the defect (e.g., a defective pattern, a particle or a scratch).

Current laser inspection techniques typically scan the wafer under inspection with laser light, and detect scattering or diffraction of the incident light by structures and defects on the wafer surface. In other words, information produced by the scattering or diffraction of light at the incident wavelength, known as "linear optical phenomena", are used to determine whether or not defects exist on the wafer surface. Linear optical phenomena are affected largely by the geometry and refractive indices of the materials on the wafer, and therefore typically yield information regarding the size and shape of surface features. This information from a site under inspection is compared with linear optical phenomena observed at a nominally identical site on the wafer or a reference site, and if the two sites do not exhibit the same optical phenomena, it is determined that a defect may exist at the inspected site.

Conventional laser inspection techniques have several shortcomings. They do not gather information directly relating to the material composition of surface features or defects that would indicate the presence of an unwanted foreign material. Additionally, they typically do not reliably detect small defects that scatter a limited amount of light, since the light scattered by a small defect can be lost in the light scattered by features, such as patterns, on the wafer surface proximal to the defect. Thus, a small defect may not be detected at all, depending on its location on the wafer surface. The limited accuracy and scope of conventional laser inspection lowers manufacturing yield and increases production costs.

Further information is obtainable from a laser inspection of wafer surface, especially information relating to chemical composition and interfaces between materials, by observing nonlinear optical effects, broadly defined as those in which the radiation emanating from the illuminated region of the wafer contains wavelengths other than that of the incident radiation. Potentially useful nonlinear optical phenomena include photoluminescence (also known as "fluorescence"), Raman scattering and second harmonic generation. However, although fluorescence microscopes and scanning Raman microscopes are commercially available; e.g., for studying biological samples and contaminants at the defect review stage, such systems are not suitable for high-throughput semiconductor wafer inspection. They are not designed to scan an entire wafer, but rather to image isolated small regions, and their scan speed is incompatible with the throughput required of an automated wafer inspection system. Moreover, they do not incorporate the requisite wafer handling systems, defect detection electronics and algorithms.

There exists a need for a methodology and apparatus for in-process inspection of semiconductor wafers that provides information relating to the material composition and interfaces between materials of surface features and defects. This need is becoming more critical as the density of surface features, die sizes, and number of layers in semiconductor devices increase, requiring the number of defects to be drastically reduced to attain an acceptable manufacturing yield.

SUMMARY OF THE INVENTION

An advantage of the present invention is a method and apparatus for optical inspection of semiconductor wafers that obtains information relating to the chemical composition and interfaces between materials simultaneously with obtaining topographical and feature size information, thereby enabling fast, reliable and comprehensive defect detection.

Additional advantages and other features of the present invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing and other advantages are achieved in part by an apparatus for inspecting a surface of an article, the apparatus comprising a light source for irradiating a portion of the surface of the article with a light beam at an incident wavelength; a first detector for receiving light at the incident wavelength from the portion of the surface and generating a first signal; a second detector for receiving light at a wavelength different from the incident wavelength from the portion of the surface and generating a second signal; and a processor configured for determining, based on the first and second signals, whether a defect exists on the portion of the surface.

Another aspect of the present invention is a method for inspecting a surface of an article, the method comprising irradiating a portion of the surface of the article with a light beam at an incident wavelength; receiving light at the incident wavelength from the portion of the surface at a first detector to generate a first signal; receiving light at a wavelength different from the incident wavelength from the portion of the surface at a second detector to generate a second signal; and determining whether a defect exists on the portion of the surface based on the first and second signals.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

Reference is made to the attached drawings, wherein elements having the same reference numeral designations represent like elements throughout, and wherein.

DESCRIPTION OF THE INVENTION

Figure 1:
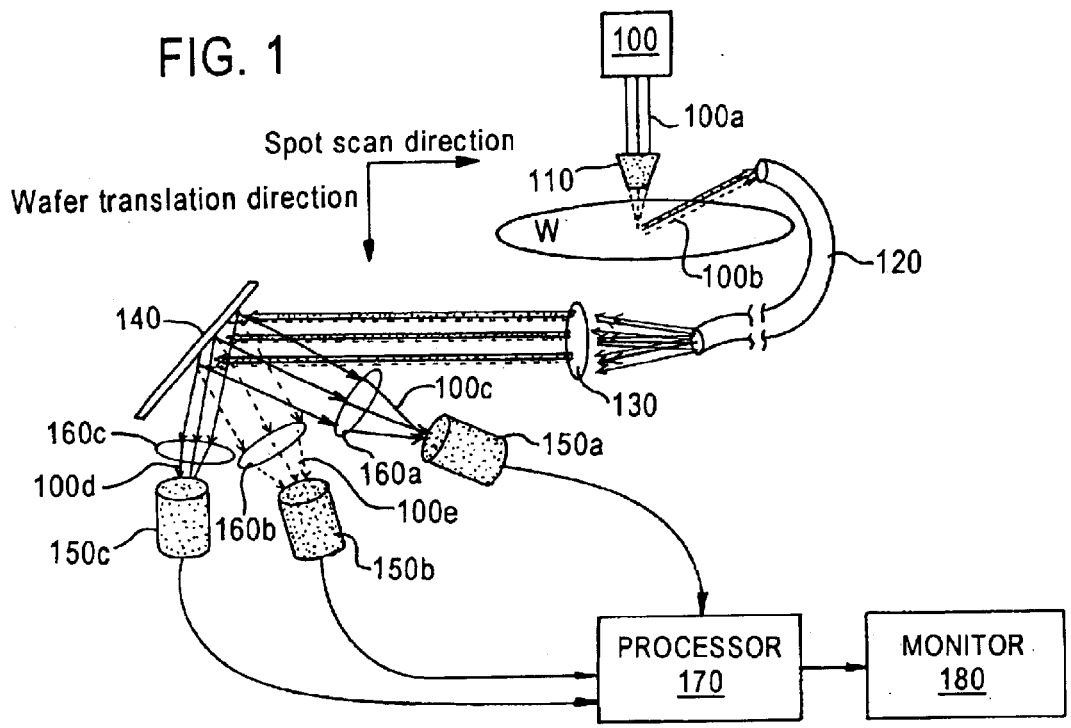
FIG. 1 illustrates an inspection apparatus in accordance with an embodiment of the present invention.

Conventional optical inspection tools used to detect defects in semiconductor wafers process only linear optical phenomena, which yield primarily topographical information relating to features and defects. However, conventional inspection tools cannot readily discover and incorporate information relating to chemical composition and material interfaces into their defect detection and classification techniques, since they do not process nonlinear optical phenomena. As a result, conventional optical inspection tools can fail to detect certain types of defects, and cannot classify defects with the speed and precision required by current ultra large scale integration processes. The present invention addresses and solves these problems stemming from conventional optical inspection techniques.

According to the methodology of the present invention, a portion of the surface of a semiconductor device is irradiated with a light beam, such as a conventional scanning laser, at an incident wavelength. The light emanating from the irradiated surface portion is then separated into light at the incident wavelength and light at one or more predetermined non-incident wavelengths, as by a diffraction grating, prism or filters. The light at the incident wavelength is sent to a detector, such as a conventional photomultiplier (PMT), which converts the detected linear optical phenomena (representing, e.g., surface topography), into an electrical signal. Likewise, the separated light at the non-incident wavelength (or wavelengths) is sent to a discrete detector (or detectors), such as a PMT, which converts the detected nonlinear optical phenomena, such as fluorescence, Raman scattering and/or second harmonic generation, into an electrical signal (or signals) representing, e.g., chemical composition and material interfaces. The signal from each detector is sent to a processor, which generates a defect map based on the information gleaned from both the linear and nonlinear optical phenomena, as by comparing data from the inspected site on the wafer with corresponding data from a theoretically identical site. Because the present invention utilizes linear and nonlinear optical phenomena to detect defects based not only on the topography and size of wafer surface features, as do conventional optical inspection tools, but also based on chemical composition and interfaces between materials, defects can be detected with greater accuracy and classified with greater precision. Moreover, since the linear and nonlinear optical data are gathered simultaneously, the present invention does not increase inspection time.

Well-known nonlinear optical phenomena utilized in practicing the present invention can include, but are not limited to, fluorescence, Raman scattering, and second harmonic generation. Fluorescence, also known as photoluminescence ("PL"), occurs when a material is irradiated, as with laser light, to excite electrons in the material, and the excited electrons relax back to their ground state emitting a photon which can be detected by a PMT. The wavelength of PL varies with different materials. For example, many materials found in standard semiconductor device technology, such as bulk silicon, aluminum, copper, tungsten, and silicon dioxide, do not exhibit PL or produce very weak PL radiation. On the other hand, certain chemical compounds or nanostructures produced at interfaces of these materials, such as metal oxides, metal-doped glasses, and nanoparticles of silicon in silicon dioxide, are known to generate relatively large amounts of PL, especially under excitation by ultraviolet (UV) light. Certain organic compounds used in photoresist for wafer patterning also emit strong PL.

In practicing the present invention utilizing PL, if a laser-scanned site on the surface of an inspected wafer exhibits PL above an acceptable background or threshold level, and a corresponding reference site does not, it can be inferred that a material is present on the inspected wafer that should not be present. Alternatively, if the inspected site exhibits PL at a different wavelength than expected, it can be inferred that a defect exists at the inspected site. Generally, the user will employ one or more detectors to monitor one or more spectral bands, depending on their situation, materials, and experience with their process. As discussed in further detail below, if several PL wavelengths are to be monitored, one detector can be set to detect all the wavelengths; however, it may be advantageous to monitor several wavelengths separately using a plurality of detectors.

The nonlinear optical phenomenon of Raman scattering occurs due to interactions between photons entering a material and other basic excitations in the material, such as vibrational excitations of its molecules, that result in the emission of "phonons". These interactions between photons and phonons occur because electrons and charged particles are both coupled to the molecules of the material. Raman scattering is a result of the interaction between a photon, which is a vibration of an electric field, and a phonon, which is a vibration of an atom at a specific frequency. In Raman scattering, the energy of a "Stokes-shifted" photon that emanates from a material (i.e., the scattered light) is equal to the energy of the photon entering the material less the energy of the excited phonon; in other words, the energy the entering photon gave up to the vibration of the phonon. This phenomenon is known as a "Raman shift" of wavelength and yields very sharp spectral lines.

Most solids and liquids produce Raman lines, but the intensity of these lines is typically extremely weak. However, Raman scattering is greatly enhanced when the excited region is proximal to metal exhibiting resonances close to the wavelength of the exciting and/or emitted light. Thus, Raman scattering phenomena are useful for inspecting metal structures in semiconductor devices, and for inspecting for foreign materials. For example, if a portion of a metal contact formed in a wafer is missing, or the wafer is contaminated by a metal, these defects can be detected by observing Raman scattering.

Second harmonic generation (SHG) occurs when two photons entering a material simultaneously excite an electron. The excited electron immediately relaxes, emitting a photon of twice the energy of a single photon. For example, two photons of 1 eV each enter a material, and one photon of 2 eV is emitted; that is, the emitted photon has a different wavelength than the incoming photons. SHG does not occur in the bulk materials commonly used in semiconductor manufacturing, such as bulk silicon and silicon dioxide, due to their crystalline symmetries. However, structures and interfaces break crystalline symmetries that prevent SHG. Therefore, SHG is useful in characterizing doping levels of silicon layers and interfaces between layers. In the methodology of the present invention, the presence or absence of SHG is used to determine if a defect is present; e.g., if an interface is missing, expected SHG will be missing.

An inspection apparatus according to an embodiment of the present invention is illustrated in FIG. 1, and comprises a conventional laser source 100 for irradiating wafer W with a laser beam 100a at an incident wavelength and scanning it across the surface of wafer W. Laser beam 100a is either continuous wave (CW) or modelocked (i.e., short pulse) and can be one of a number of wavelengths depending on the optical phenomenon to be exploited and the optimal excitation energy of the materials to be inspected, as explained below. Laser source 100 uses a well-known rapidly scanning laser spot technique, wherein laser beam 100a is focused into a spot by an objective lens system 110 to irradiate a small portion of wafer W. Laser beam 100a's spot is scanned, using well-known techniques, as in the x-direction, across the surface of wafer W in a straight line. Wafer W is then moved, as in the y-direction, and another line is scanned.

Laser beam 100a impinges on wafer W, and scattered light 100b from wafer W is directed in a conventional manner, as by a fiber optic tube 120 and collimating lens 130, to a diffraction grating 140, such as available from Jobin-Yvon Inc., U.S.A., which separates scattered light 100b into scattered light 100c at the incident wavelength and scattered light 100d, 100e at wavelengths other than the incident wavelength. Alternatively, a prism (not shown) can be used instead of diffraction grating 140 for separating scattered light 100b. Separated scattered light 100c at the incident wavelength is relayed by diffraction grating 140 to detector 150a, as through lens 160a, in a conventional manner. Likewise, separated scattered light 100d, 100e at wavelengths other than the incident wavelength is relayed to detectors 150b, 150c, as through lenses 160b, 160c. Lenses 130 and 160a, 130 and 160b, 130 and 160c serve as relay pairs to ensure a stationary spot on the detectors 150a–c and a collimated beam at diffraction grating 140. Detectors 150a–c are standard PMT's, as are available from Hamamatsu of Japan. PMTs are substantially similar in operation; filters or gratings used with them determine what wavelength of light is detected. Additionally, since stray light at the incident wavelength can be strong enough to prevent accurate gathering of the scattered light at other wavelengths 100d, 100e, blocking filters (not shown) are preferably placed in from of detectors 150a, 150b.

Each detector 150a–c generates an electrical signal responsive to the light directed to it. The electrical signals are sent to a processor 170, such as an electronic computer, which determines whether a defect exists at the scanned portion of wafer W by comparing the signals from detectors 150a–c with signals collected from a theoretically identical reference site, such as another site on the surface of wafer W, in a conventional manner. For example, it can be determined that a defect exists when a signal from a detector collecting emissions at a wavelength other than incident from the inspected site is above a threshold level while the corresponding signal from the reference site is at or below the threshold level. Well-known statistical methods can also be employed to produce a defect map showing suspected locations on the wafer having a high probability of a defect. The results of processor 170's operations are displayed on a monitor 180.

In a further embodiment of the present invention, defects are detected and automatically classified based on their optical emission properties. In this embodiment, it is determined that a defect exists when a signal from a detector collecting emissions at a particular wavelength other than incident from the inspected site is above a threshold level, indicating the presence of a particular unwanted foreign material. That defect is then automatically classified by processor 170, thus eliminating the need for employment of a review tool to classify the defect, thereby reducing inspection time. For example, the present invention can immediately identify a particle of photoresist on an otherwise clean wafer surface, thereby pointing to the defect source without additional review.

A further advantage of the present invention is the ability to discriminate optical signals, and thus defects, from different layers by analyzing signals from multiple layers such that the signal from an underlying pattern is removed along with its associated noise, enabling defect analysis of the upper layer, or vice versa. For example, a fluorescence signal can arise primarily from photoresist and not from the substrate beneath the photoresist, while the linear scattering from layers beneath the photoresist can dominate and thereby obscure the linear signal from the photoresist. Thus, the present invention enables the photoresist to be readily "seen" and analyzed by analyzing its fluorescence signal.

While FIG. 1 shows one detector 150a for collecting scattered light at the incident wavelength and two detectors 150b, 150c for collecting scattered light at wavelengths other than the incident wavelength in two spectral bands, the present invention is not limited to three detectors. For example, a plurality of detectors can be provided at different collection angles for collecting scattered light at the incident wavelength, and for collecting scattered light at wavelengths other than the incident wavelength depending on the number of wavelengths to be collected. For a typical high-throughput wafer inspection system, the nonlinear spectral channels can be optimized by 1) limiting the number of spectral channels to maximize weak nonlinear optical signals by integrating over a relatively large spectral range; 2) limiting the number of spectral channels to minimize the data processing overhead, which is typically significant for each additional data channel; and 3) providing a sufficient number of spectral channels to resolve a desired number of different defect sources.

The apparatus of FIG. 1 can utilize many components of a current conventional laser scanning wafer inspection tool, such as a Model "Compass", available from Applied Materials of Santa Clara, Calif., including laser source 100, lenses 110, 130, 160a–c, detectors 150a–c, processor 170 and monitor 180, with the addition of diffraction grating 140 for separating collected light 100b into the desired wavelengths. Of course, one skilled in the art would appreciate that detectors 150b, 150c must be provided in sufficient number and adjusted to detect the desired non-incident wavelengths, and processor 170 must be programmed to process the signals from detectors 150b, 150c corresponding to nonlinear optical phenomena and generate a defect map incorporating the results.

The apparatus of FIG. 1 is especially suitable for detecting PL and Raman scattering. In general, a CW or modelocked deep ultraviolet (DUV) laser source is desirable to excite PL, although for some materials a longer wavelength is optimal. The Raman cross-section increases with the third power of the laser frequency, so a DUV source is also suitable for detecting Raman scattering. However, as discussed above, in the case where proximity to a resonant plasmon is expected to enhance the Raman emission, a wavelength in the vicinity of the plasmon resonance is required to take advantage of this phenomenon. Moreover, the bulk plasmon of metals can be in the visible to ultraviolet range, but is at lower frequencies (i.e., in the near infrared to visible spectrum) for small metallic particles.

The rapidly scanning laser spot technique of laser source 100 is suitable for detecting nonlinear optical phenomena, such as Raman scattering, SHG and fluoresence, that decay on time scales shorter than the scanner's pixel sampling time; i.e., the dwell time of laser beam 100a at any portion of wafer W (typically about 10 nanoseconds). It must be used to detect SHG, because the strength of the second harmonic signal is dependent upon the square of the intensity of the incident light. Thus, a tightly focused light beam, as provided in the rapidly scanning laser spot technique, produces the best results.

Figure 2:
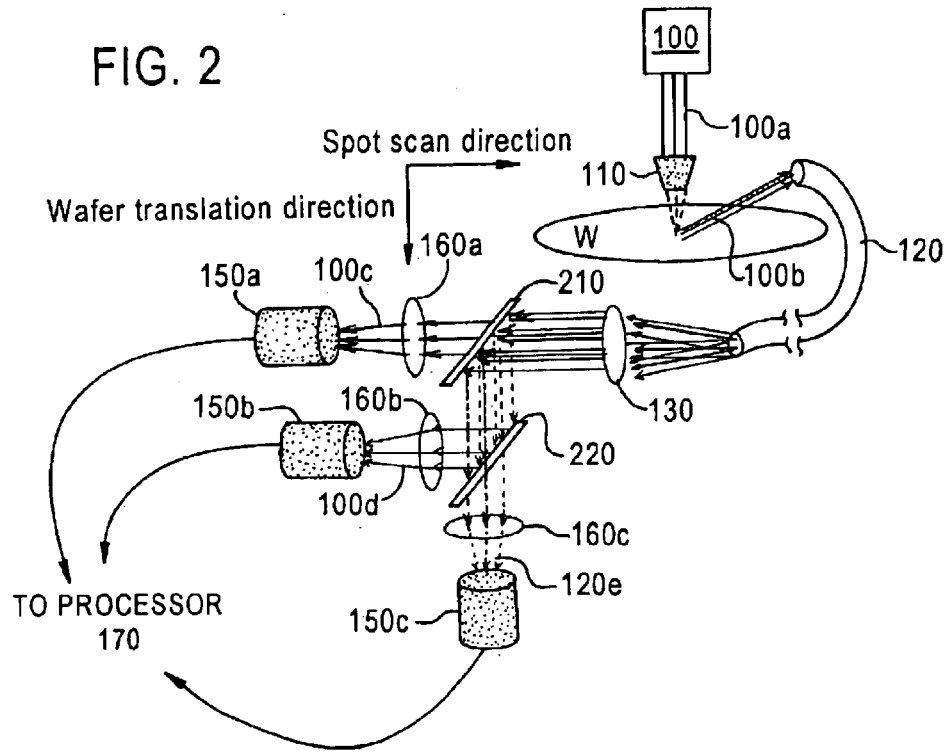
FIG. 2 illustrates an inspection apparatus in accordance with another embodiment of the present invention.

In another embodiment of the present invention, illustrated in FIG. 2, an inspection apparatus is provided that is substantially identical to the apparatus of FIG. 1, except that diffraction grating 140 is replaced with successive conventional dichroic mirrors 210, 220 for separating scattered light beam 100b into scattered light beams 100c–e and relaying them to detectors 150a–c. Suitable dichroic mirrors are available from Omega Optical Corp., U.S.A. Dichroic mirror 210 allows scattered light at the incident wavelength 100c to pass through it to detector 150a, and reflects light at wavelengths other than the incident wavelength to dichroic mirror 220, which separates the light at the non-incident wavelengths into predetermined spectral bands 100d–e and relays them to detectors 150b–c. Alternatively, conventional bandpass filters can be used instead of or along with dichroic mirrors 210, 220 to separate scattered light 100b into several spectral bands as required.

The embodiments of the present invention shown in FIGS. 1 and 2 separate scattered light 100b in the "dark field"; that is, in a direction other than the specularly reflected direction. In an apparatus according to a further embodiment of the present invention, illustrated in FIG. 3, separation of scattered light is performed in the "bright field"; in other words, scattered light 100b is collected by the same objective 310 used to illuminate wafer W. The nonlinear spectral bands 100c, 100d are separated by dichroic mirrors 320, 330, and lenses 340a–c and relayed to detectors 350a–b. Alternatively, a diffraction grating, prism, or bandpass filters as described with reference to the embodiments of FIGS. 1 and 2 can be used instead of dichroic mirrors 320, 330 for separating and relaying the nonlinear spectral bands.

Figure 3:
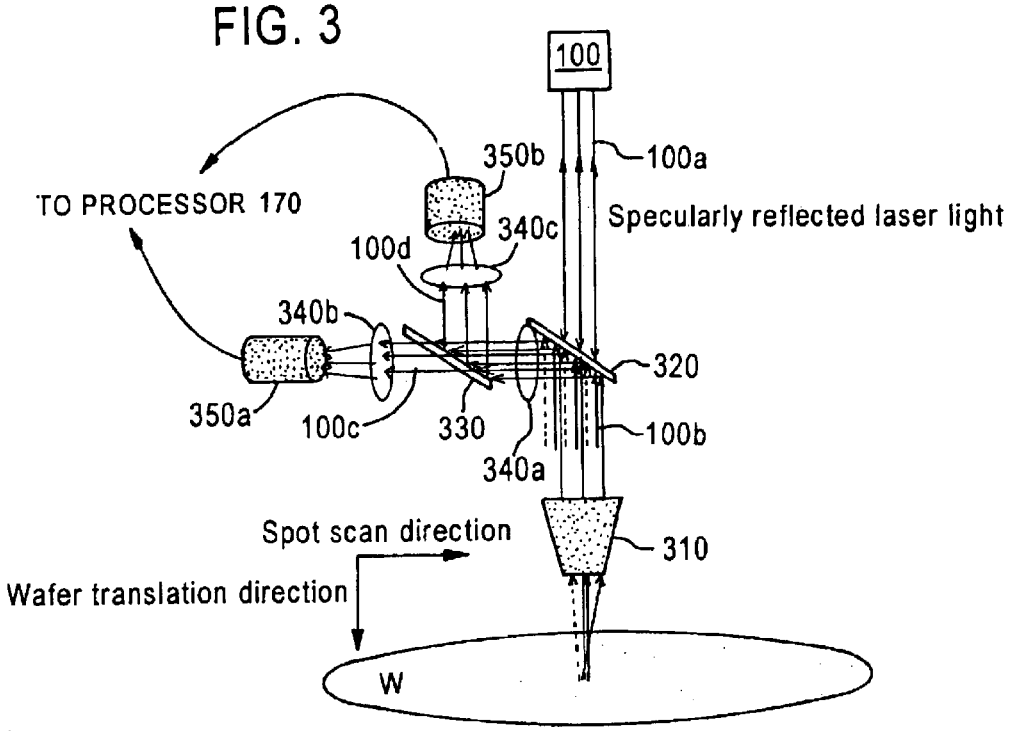
FIG. 3 illustrates an inspection apparatus in accordance with another embodiment of the present invention.

The bright field detection scheme of the apparatus of FIG. 3 has the advantage of enabling a relatively large collection aperture for the nonlinear radiation, depending on configuration of objective 310. For example, for a spectrally broad application, an optimal objective 310 would be based on all-reflective optics. However, when only Raman scattering is expected, such an objective would not be particularly advantageous.

While the bright field configuration of FIG. 3 is suitable for detection of Raman scattering and PL, it is highly effective for collecting SHG, since SHG is a coherent process wherein the "upconverted" light (i.e., the high-energy emitted photon) follows the path of the incident light. Since most of the incident light is typically specularly reflected from wafer W back into objective 310, the SHG will also be collected primarily by objective 310.

An inspection apparatus according to a further embodiment of the present invention will now be described with reference to FIG. 4. This embodiment of the present invention utilizes the well-known scanning laser line technique, wherein a laser beam 400a generated by a laser source 400 is directed through a cylindrical lens 410, which focuses laser beam 400a into a line 400b for irradiating the surface of wafer W. Scanning is performed one line at a time, by moving wafer W as shown by the arrow. Thus, scanning needs to be performed in only one direction, not two, as in the spot scanning technique of the apparatus of FIGS. 1–3 (e.g., scanning is done only in the y-direction by moving wafer W, and not in the x-direction).

Scattered light 400c from wafer W is separated in the dark field into light at the incident wavelength 400d and light at wavelengths other than incident 400e, 400f by a concave diffraction grating 420, such as a Model 533 00 030 diffraction grating, available from Jobin-Yvon Inc., U.S.A. Concave grating 420 eliminates the need for lenses or mirrors. However, a flat diffraction grating with auxiliary optics can be used instead of a curved grating 420. Separated scattered light 400d–f is relayed to linear detector arrays 430a–c, typically semiconductor detectors comprising charge coupled devices (CCDs), such as Model S3903 linear detector arrays, available from Hammamatsu of Japan. The scattered laser light line 400c is imaged onto one linear detector array for each spectral band to be detected, in order to preserve spatial resolution.

Figure 4:
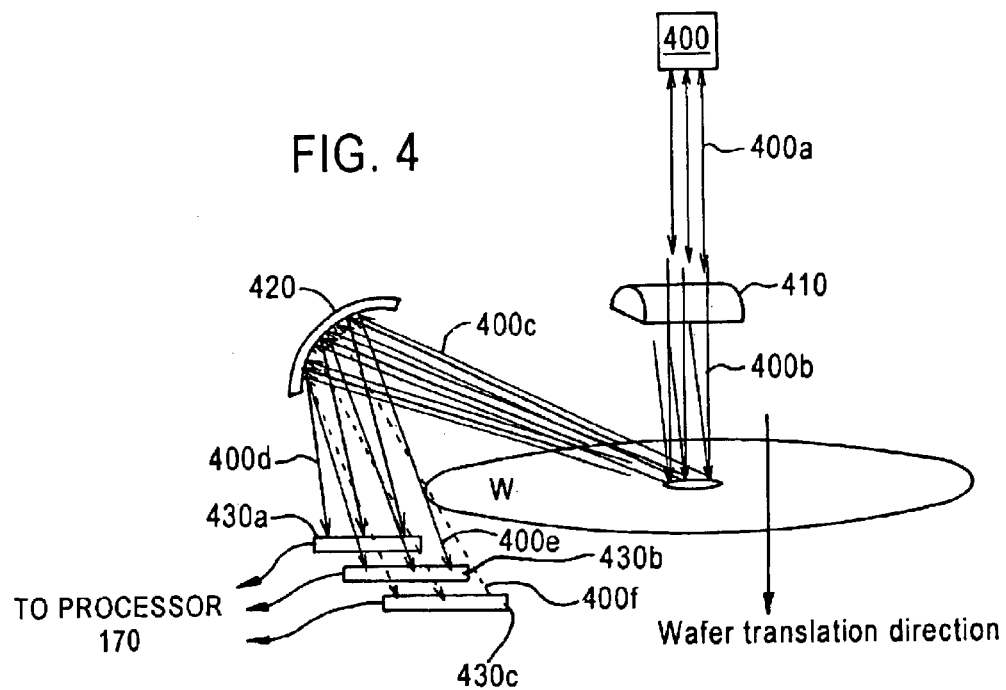
FIG. 4 illustrates an inspection apparatus in accordance with another embodiment of the present invention.

The scanning laser line technique of the apparatus of FIG. 4 increases the pixel sampling time by about 2–3 orders of magnitude compared with the pixel sampling time of the flying laser spot technique of the apparatus of FIGS. 1–3, since the laser is not scanned laterally. Therefore, the scanning laser line technique is useful for detecting nonlinear optical phenomena having a decay time longer than the pixel sampling time of the flying laser spot technique, such as phosphorescence. It is also advantageous in that it requires a simpler scanning mechanism than the flying laser spot technique. Moreover, due to the reduced laser intensity at the wafer, the scanning laser line technique eliminates possible damage to the wafer under inspection induced by high instantaneous radiation. However, since the laser intensity at the wafer is low, the scanning laser line technique is not suitable for detecting SHG and other optical phenomena which scale superlinearly with the incident intensity.

Figure 5:
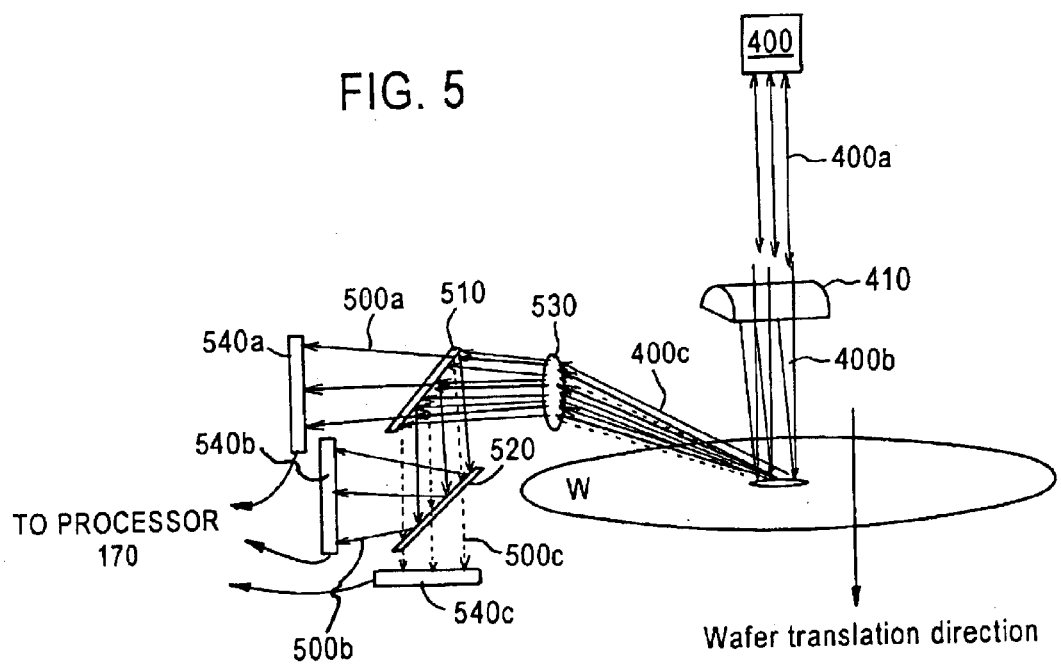
FIG. 5 illustrates an inspection apparatus in accordance with another embodiment of the present invention.

Another embodiment of the present invention is illustrated in FIG. 5, wherein an inspection apparatus is provided that is substantially identical to the scanning laser line, dark field apparatus of FIG. 4, except that concave diffraction grating 420 is replaced with successive conventional dichroic mirrors 510, 520 for separating scattered light beam 400c into scattered light beams 500a–c and relaying them to linear detector arrays 540a–c. Suitable dichroic mirrors are available from Omega Optical Corp., U.S.A. Lens 530 images scattered light line 400c onto linear detector arrays 540a–c. Dichroic mirror 510 allows scattered light at the incident wavelength 500a to pass through it to detector array 540a, and reflects light at wavelengths other than the incident wavelength to dichroic mirror 520, which separates the light at the non-incident wavelengths into predetermined spectral bands 500b–c and relays them to detector arrays 540b–c.

Figure 6:
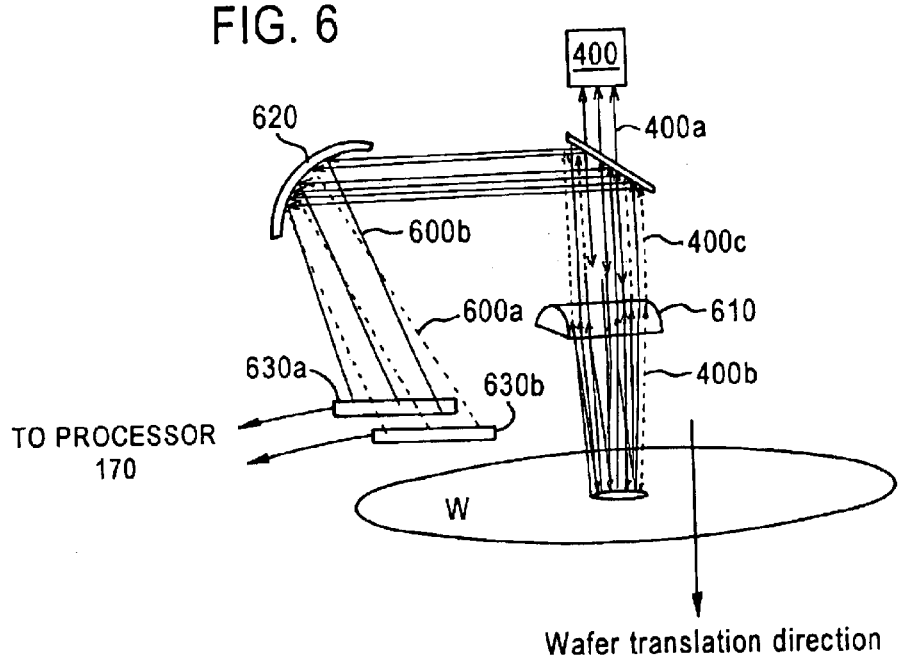
FIG. 6 illustrates an inspection apparatus in accordance with another embodiment of the present invention.

FIG. 6 illustrates an apparatus according to the present invention utilizing the scanning laser line technique along with a bright field configuration. Laser beam 400a generated by laser source 400 is directed through a cylindrical lens 610, which focuses laser beam 400a into a line 400b for irradiating the surface of wafer W. Scanning is performed one line at a time, as in the embodiments of FIGS. 4 and 5. Scattered light 400c is collected by the prism 610, and the nonlinear spectral bands 600a, 600b are separated by concave diffraction grating 620 and relayed to linear detector arrays 630a, 630b. Alternatively, dichroic mirrors or bandpass filters as described with reference to the embodiment of FIG. 5 can be used instead of diffraction grating 620 for separating and relaying the nonlinear spectral bands.

Similarly to the embodiment of FIG. 3 discussed above, the bright field detection scheme of the apparatus of FIG. 6 has the advantage of enabling a relatively large collection aperture for the nonlinear radiation, depending on configuration of objective 610. Thus, for a spectrally broad application, an optimal objective 610 would be based on all-reflective optics, but such optics would not be advantageous when only Raman scattering is expected.

Figure 7:
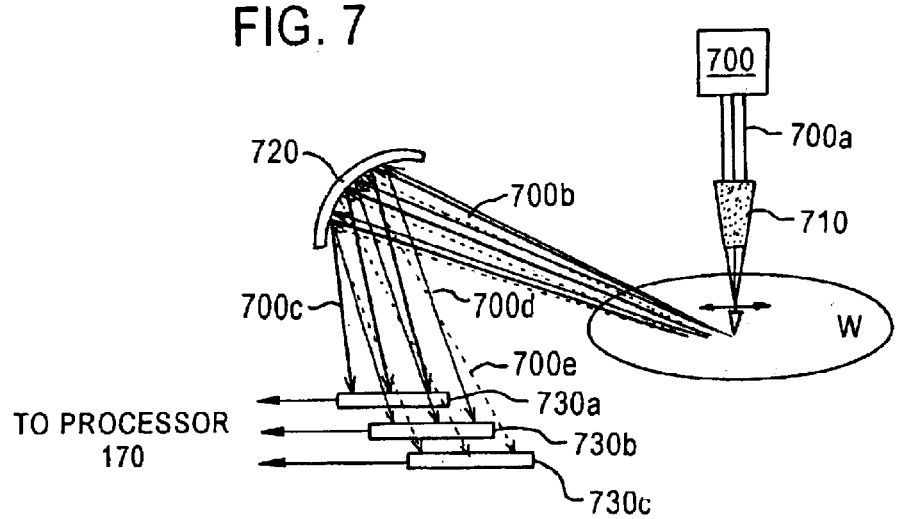
FIG. 7 illustrates an inspection apparatus in accordance with another embodiment of the present invention.
Figure 8:
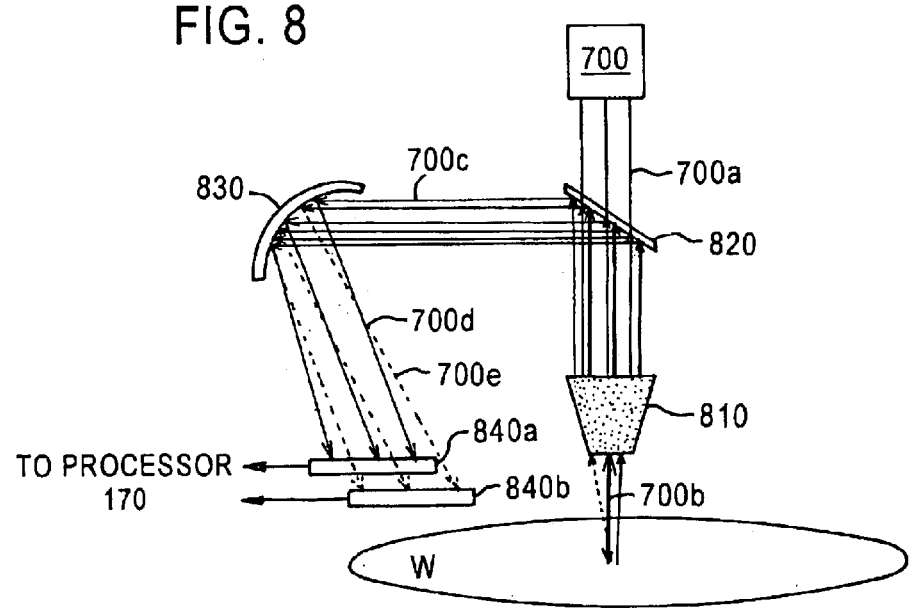
FIG. 8 illustrates an inspection apparatus in accordance with another embodiment of the present invention.

In further embodiments of the present invention, illustrated in FIGS. 7 and 8, the flying laser spot configuration of the embodiments of FIGS. 1–3 is combined with a concave diffraction grating and linear detector arrays. Referring now to FIG. 7, a conventional laser source 700 as described above is provided for irradiating wafer W with a laser beam 700a at an incident wavelength and scanning it across the surface of wafer W. Objective lens 710 focuses laser beam 700a to a spot. Scattered light 700b from wafer W in the dark field impinges on a concave diffraction grating as described in the embodiment of FIG. 4, which separates scattered light 700b into scattered light at the incident wavelength 700c that is relayed to a linear detector array 730a, and scattered light at wavelengths other than the incident wavelength 700d, 700e, which are relayed to linear detector arrays 730b, 730c.

FIG. 8 shows an inspection apparatus according to the present invention similar to that of FIG. 7, except that the scattered light is collected in the bright field. Laser source 700 irradiates wafer W with laser beam 700a through objective 810. Scattered light 700b is collected through objective 810 and relayed to a conventional dichroic mirror 820 that reflects scattered light not at the incident wavelength 700c to concave diffraction grating 830, which further separates scattered light 700c into the desired spectral bands 700d, 700e and relays it to linear detector arrays 840a, 840b.

The inspection apparatus of FIGS. 7 and 8 is advantageous for detecting nonlinear optical phenomena having long decay times that would cause loss of spatial resolution if PMTs and a flying laser spot scanning technique were employed together, as in the embodiments of FIGS. 1–3. In the apparatus of FIGS. 7 and 8, the laser spot generated by laser source 700 scans rapidly, but the resultant scan line is imaged onto photodetector arrays 730a–c, 840a–b, rather than onto PMTs. Since each detector in each array receives light only once every time a line of spots on wafer W is scanned, the scan line can be integrated over a time scale long enough to allow the light to decay before another scan line is imaged, thereby insuring good spatial resolution.

The present invention is applicable to the manufacture of various types of semiconductor devices, particularly high-density semiconductor devices having a design rule of about 0.18 $\mu$ and under.

The present invention can be practiced by employing conventional materials, methodology and equipment. Accordingly, the details of such materials, equipment and methodology are not set forth herein in detail. In the previous descriptions, numerous specific details are set forth, such as specific materials, structures, chemicals, processes, etc., in order to provide a thorough understanding of the present invention. However, it should be recognized that the present invention can be practiced without resorting to the details specifically set forth. In other instances, well known processing structures have not been described in detail, in order not to unnecessarily obscure the present invention.

Only the preferred embodiment of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. An apparatus for inspecting a surface of an article, the apparatus comprising:
    a light source for irradiating a portion of the surface of the article with a light beam at an incident wavelength;
    a first detector for receiving light at the incident wavelength from the portion of the surface and generating a first signal responsive to the light at the incident wavelength;
    a second detector for receiving light at a wavelength different from the incident wavelength from the portion of the surface and generating a second signal responsive to the light at the wavelength different from the incident wavelength;
    a scanner for scanning the light beam across the surface of the article from the portion of the surface to another portion of the surface; and
    a processor configured for determining, based on both the first and second signals, whether a defect exists on the scanned portions of the surface, and for generating a single defect map of the surface of the article based on the processor's defect determination.

2. The apparatus of claim 1, wherein the light source is a laser for producing laser light at the incident-wavelength.

3. The apparatus of claim 2, wherein the laser provides continuous wave laser light or modelocked laser light.

4. The apparatus of claim 2, wherein the scanner is for scanning the laser light across the surface of the article from the portion of the surface to the other portion of the surface.

5. The apparatus of claim 4, wherein the scanner is for focusing the laser light to a spot and rapidly scanning the spot across the surface of the article.

6. The apparatus of claim 4, wherein the scanner is for focusing the laser light to a line.

7. The apparatus of claim 6, wherein the first and second detectors comprise a linear detector array comprising semiconductor detectors.

8. The apparatus of claim 1, wherein the second detector is for detecting fluorescence from the portion of the surface.

9. The apparatus of claim 1, wherein the second detector is for detecting Raman scattering from the portion of the surface.

10. The apparatus of claim 1, wherein the second detector is for detecting second harmonic generation.

11. The apparatus of claim 1, wherein the first and second detectors comprise photomultipliers.

12. The apparatus of claim 1, comprising a separator disposed between the surface of the article and the first and second detectors, for separating the light from the portion of the surface at the incident wavelength from the light at the other wavelength and directing the light to the first and second detectors.

13. The apparatus of claim 12, wherein the separator comprises a diffraction grating.

14. The apparatus of claim 12, wherein the separator comprises a cylindrical lens.

15. The apparatus of claim 12, wherein the separator comprises a bandpass filter.

16. The apparatus of claim 12, wherein the separator comprises a focusing lens.

17. The apparatus of claim 12, wherein the separator comprises a plurality of dichroic mirrors.

18. The apparatus of claim 12, further comprising an objective lens between the light source and the surface of the article.

19. The apparatus of claim 18, wherein the objective lens is for passing the light from the portion of the surface of the article to the separator.

20. An apparatus for inspecting a surface of an article, the apparatus comprising:
a light source for irradiating a portion of the surface of the article with a light beam at an incident wavelength;
a plurality of first detectors for receiving light at the incident wavelength from the portion of the surface and generating first signals responsive to the light at the incident wavelength;
a plurality of second detectors for receiving light at a wavelength different from the incident wavelength from the portion of the surface and generating second signals responsive to the light at the wavelength different from the incident wavelength; and
a scanner for scanning the light beam across the surface of the article from the portion of the surface to another portion of the surface, and
a processor configured for determining, based on all of the first and second signals, whether a defect exists on the scanned portions of the surface, and for generating a single defect map of the surface of the article based on the processor's defect determination.

21. A method for inspecting a surface of an article, the method comprising:
irradiating a portion of the surface of the article with a light beam at an incident wavelength;
receiving light at the incident wavelength from the portion of the surface at a first detector to generate a first signal responsive to the light at the incident wavelength;
receiving light at a wavelength different from the incident wavelength from the portion of the surface at a second detector to generate a second signal responsive to the light at the wavelength different from the incident wavelength; and
scanning the light beam across the surface of the article from the portion of the surface to another portion of the surface;
determining whether a defect exists on the scanned portions of the surface based on both the first and second signals; and
generating a single defect man of the surface of the article based on the defect determination.

22. The method of claim 21 comprising focusing the light beam to a spot and rapidly scanning the spot across the surface of the article.

23. The method of claim 21 comprising focusing the light beam to a line.

24. The method of claim 21, comprising detecting fluorescence from the portion of the surface with the second detector.

25. The method of claim 21, comprising detecting Raman scattering from the portion of the surface with the second detector.

26. The method of claim 21, comprising detecting second harmonic generation from the portion of the surface with the second detector.

27. The method of claim 21, comprising separating the light from the portion of the surface at the incident wavelength from the light at the other wavelength and directing the light to the first and second detectors.

28. A method for inspecting a surface of an article, the method comprising:
irradiating a portion of the surface of the article with a light beam at an incident wavelength;
receiving light at the incident wavelength from the portion of the surface at a first detector to generate a first signal responsive to the light at the incident wavelength;
receiving light at a wavelength different from the incident wavelength from the portion of the surface at a second detector to generate a second signal responsive to the light at the wavelength different from the incident wavelength;
irradiating a portion of a reference surface corresponding to the portion of the surface of the article with a second light beam at the incident wavelength;
receiving light at the incident wavelength from the portion of the reference surface at the first detector to generate a third signal;
receiving light at a wavelength different from the incident, wavelength from the portion of the reference surface at the second detector to generate a fourth signal and
determining whether a defect exists on the portion of the surface based on the second third and fourth signals.

29. The method of claim 28, comprising generating a defect map of the surface of the article based on the first, second, third and fourth signals.

30. The method of claim 28, wherein the determining step comprises determining that the defect exists when the second signal is above a threshold level and the fourth signal is below the threshold level.

31. The method of claim 21, wherein the determining step comprises determining the defect exists when the second signal is a predetermined value, the predetermined value corresponding to a particular wavelength other than the incident wavelength.

32. The method of claim 31, comprising classifying the defect into a predetermined category when the second signal is the predetermined value.

* * * * *